United States Patent [19]

Kramer et al.

[11] 4,411,652
[45] Oct. 25, 1983

[54] INTERNALLY STERILE PULSATILE INFUSOR SYSTEM

[75] Inventors: Steven G. Kramer; Edward Q. Yavitz, both of San Francisco, Calif.

[73] Assignee: The Regents of the University of California, Berkeley, Calif.

[21] Appl. No.: 295,024

[22] Filed: Aug. 21, 1981

[51] Int. Cl.³ .................. A61M 5/00; F04B 45/06
[52] U.S. Cl. ................. 604/153; 417/478;276; F04B/43/08
[58] Field of Search ............ 128/214 F, 214 E, 214, 128/66; 417/478, 276; 604/153.34, 250; 222/207

[56] References Cited

U.S. PATENT DOCUMENTS

| 3,099,429 | 7/1963 | Brown | 251/6 |
|---|---|---|---|
| 3,227,158 | 1/1966 | Mattingly | 128/66 |
| 3,589,363 | 6/1971 | Banko et al. | 128/276 |
| 3,812,855 | 5/1974 | Banko | 128/276 |
| 3,902,490 | 9/1975 | Jocobsen et al. | 128/214 F X |
| 3,942,519 | 3/1976 | Shock | 128/24 A |
| 3,995,444 | 12/1976 | Clark et al. | 62/306 |
| 4,019,514 | 4/1977 | Banko | 128/230 |
| 4,041,947 | 8/1977 | Weiss et al. | 128/276 |
| 4,108,167 | 8/1978 | Hickman et al. | 128/66 |
| 4,184,510 | 1/1980 | Murry et al. | 137/565 |
| 4,215,689 | 8/1980 | Akiyama et al. | 417/478 X |
| 4,247,288 | 1/1981 | Yoshii et al. | 433/224 |
| 4,267,833 | 5/1981 | Barger et al. | 128/214 |
| 4,274,409 | 6/1981 | Bush | 128/215 |
| 4,274,411 | 6/1981 | Dotson, Jr. | 128/276 |
| 4,290,346 | 9/1981 | Bujan | 417/478 X |

OTHER PUBLICATIONS

IBM Technical Disclosure Bulletin, Positive Displacement Pump, R. T. Albo, vol. 7, No. 11, Apr. 1965.

Primary Examiner—Stephen C. Pellegrino
Attorney, Agent, or Firm—Phillips, Moore, Lempio & Finley

[57] ABSTRACT

An internally sterile pulsatile infusor system comprises an elastic reservoir or bulb connected to a closed, sterile source of a liquid infusion solution. A check valve is connected between the source and bulb to prevent reflux of the solution therepast and a reciprocating piston is arranged to intermittently compress the bulb to create a pulsating discharge of solution through a cannula. In the preferred embodiment of this invention, controls are provided to vary the rate of compressions of the bulb and to also modulate the force of the pulsating discharge through the cannula. The pulsatile infusor system is useful in many areas in the fields of medicine and surgery, including extracapsular cataract extraction and intravenous infusion procedures wherein bloodclots and like blockages must be removed from the cannula.

16 Claims, 10 Drawing Figures

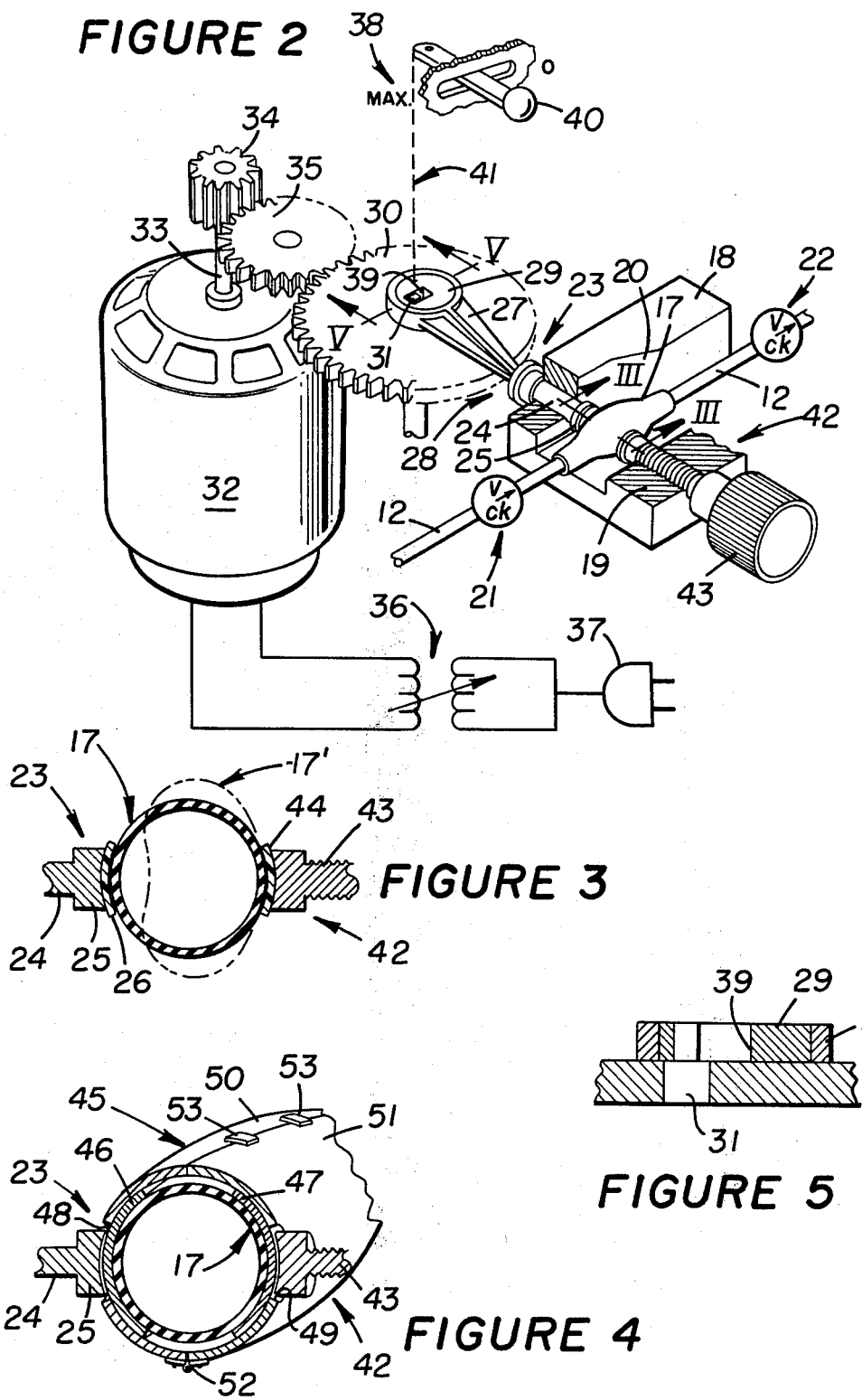

INTERNALLY STERILE PULSATILE INFUSOR SYSTEM

DESCRIPTION

1. Technical Field

This invention relates generally to a pulsatile infusor for use in the fields of medicine and surgery and more particularly to an internally sterile infusor for creating a series of pulsating discharges of a sterile liquid infusion solution through a cannula.

2. Background Art

The fields of medicine and surgery dictate the need for a highly reliable infusor adapted to discharge a sterile solution from a cannula for direct infusion or irrigation purposes. For example, during extracapsular cataract extraction the anterior capsule of the cataractous lens is opened or removed intentionally and the lens material, both cortex and nucleus, are then removed from the eye either by irrigation alone or by a combination of irrigation and aspiration. The popularity of this procedure has increased for several reasons, including improved microsurgical techniques and advanced technology for fragmenting or emulsifying lens materials, such as the Kelman phacoemulsifier and the Schock phacofragmenter. Extracapsular cataract surgery has also been found to possibly reduce the incidence of a significant post-operative complication known as aphakic cystoid macular edema. In addition, surgery of this type facilitates the implantation of a posterior chamber intraocular lens which requires that an intact posterior lens capsule be left in place in the eye following the extraction.

Since intraocular lens implantation is rapidly becoming a prevalent part of cataract extraction, an incision large enough to implant the intraocular lens in place is now required in all such procedures. The advantages of various instruments, such as the phacoemulsifier designed to maintain a very small incision approximating 3 mm., are thus severely limited. Since a larger incision in the range of 6–8 mm. or more is required for intraocular lens implantation, it has been found possible to remove the hard nucleus of the lens through this large incision relatively intact by mechanical means, not requiring sophisticated emulsifying or fragmenting equipment. Once the hard nucleus is removed, it is necessary to remove as much as possible of the relatively softer cortical material that remains, and this is conventionally done by irrigation alone or by a combination of irrigation and aspiration.

Simple continuous flow irrigation has now been found ineffective for removing much of the lens material or for adequately cleaning the intact posterior lens capsule which remains intact after the operation. Although combined irrigation and aspiration has proven more satisfactory, it has the added hazard of involving the potential for rupturing the posterior capsule, injuring the iris, and collapsing the anterior chamber with resultant injury to the corneal endothelium. Continuous flow irrigation systems of the above type are well known in the art and normally involve gravity flow or include a stripping or peristaltic pump which applies linear or rotational pressure to an elastomeric infusion line in one direction only to induce fluid flow therethrough.

Another area in the field of medicine and surgery requiring a reliable infusor is the intravenous infusion of fluids and medication. A common problem with intravenous infusion is a tendency for the infusion line to become blocked by bloodclots at the tip of the infusing needle or cannula. When the clots develop, attempts are made to reopen the line by manually causing small pulses of fluid to pass through the cannula. Frequently, this procedure has been found ineffective once the bloodclot has formed.

DISCLOSURE OF THE INVENTION

The internally sterile pulsatile infusor system embodying this invention overcomes many of the above prior art problems. The system comprises a closed sterile source of a liquid infusion solution, a conduit having its first end connected to the source to receive the solution therefrom, a cannula connected to a second end of the conduit, elastic reservoir means connected in the conduit for receiving and communicating the solution to the cannula, check valve means in the conduit for permitting solution flow only from the source to the elastic reservoir means, compression means for intermittently compressing the elastic reservoir means to create a series of pulsating discharges of solution through the cannula and rate control means for selectively varying the rate of compression of the compression means.

In one aspect of this invention, the rate control means includes variable means for varying the rate of compressions within the approximate range of from 0 to 10 compressions per second.

In another aspect of this invention, the compression means includes a reciprocal piston for periodically compressing the elastic reservoir means and stroke control means for selectively varying the length of the piston's stroke.

In still another aspect of this invention, a reciprocal piston for periodically compressing the elastic reservoir means is driven by an electric motor connected to the piston through a cam and crank arrangement.

The internally sterile pulsatile infusor system finds wide application in the fields of medicine and surgery. For example, the system can be used during extracapsular cataract extraction for irrigation and aspiration or simple irrigation purposes to remove cataractous lens material from an eye. The system may also be used for the continuous intravenous infusion of fluids and medication into a patient and for selectively pulsating fluid flow to prevent bloodclots from forming at the tip of the cannula. In particular, the system in its preferred form can be adjusted to vary the rate of compressions of the compression means in the range of from 0–10 compressions per second, for example. An experimental, working embodiment of this invention has proven its workability and commercial potential.

BRIEF DESCRIPTION OF THE DRAWINGS

Other objects and advantages of this invention will become apparent from the following description and accompanying drawings wherein:

FIG. 1 illustrates an internally sterile pulsatile infusion system embodying this invention and adapted to discharge a sterile liquid infusion solution in a controlled manner;

FIG. 2 schematically illustrates a portion of the pulsatile infusion system, including an elastic reservoir and control means for selectively varying the rate of compression of the reservoir and for modulating the force of the pulsating discharge of the liquid infusion solution;

FIG. 3 is a sectional view through the reservoir, taken in the direction of arrows III—III in FIG. 2;

FIG. 4 is a view similar to FIG. 3, but illustrates a modification of the reservoir and attendant structures;

FIG. 5 is a sectional view taken in the direction of arrows V—V in FIG. 2; and

FIGS. 6A-6E graphically illustrate pressure-time curves reflecting various tests conducted with the pulsatile infusion system of this invention.

BEST MODE OF CARRYING OUT THE INVENTION

Figure 1:
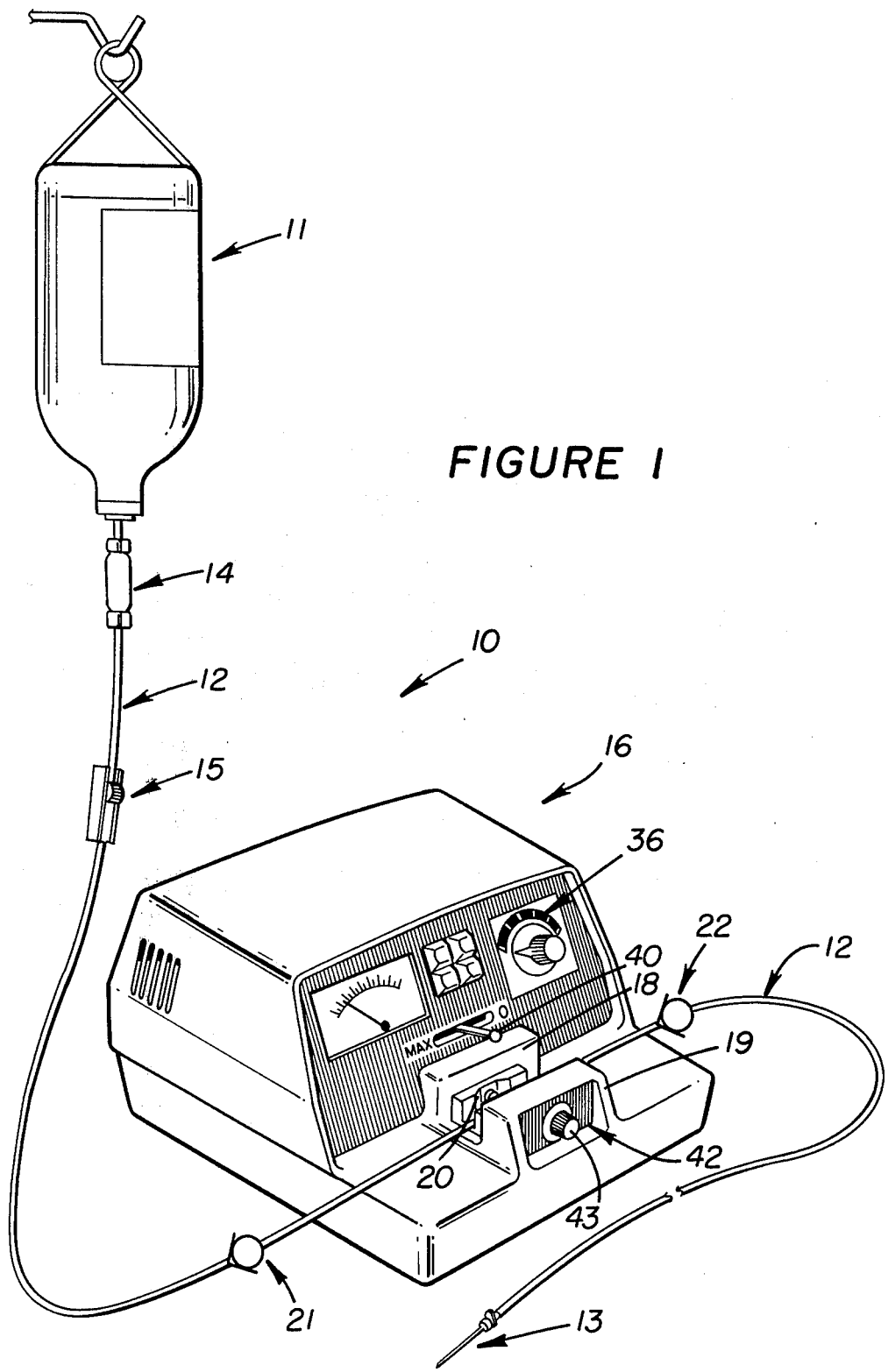

FIG. 1 illustrates an internally sterile pulsatile infusor system 10 comprising a closed, sterile source of a liquid infusion solution 11, such as a bottle or bag mounted on a hook in a conventional manner. A conduit 12 is in the form of standard flexible tubing composed of plastic or silicon rubber connected at its first end to source 11 and at its second end to a detachable infusion cannula or needle 13. The cannula is preferably connected to the tubing by a luer-lock release mechanism or the like to facilitate the attachment of various types of cannulae or needles to the tubing.

A standard drop reservoir 14 is preferably connected in the tubing to filter-out any contaminants that might be inadvertently mixed into the infusion solution. In addition, a standard roller clamp 15 is preferably connected to the tubing to compress the tubing selectively to vary the rate at which the fluid is dispensed by gravity feed. As described more fully hereinafter, the tubing extends through a control module or console 16 which functions to control the rate at which the infusion solution is pulsated through cannula 13 and to further control the magnitude of force of the pulsating discharge.

Referring to FIG. 2, the system further comprises an elastic reservoir means or elastomeric bulb 17 connected in tubing 12 to receive the infusion solution from source 11 by gravity feed and to communicate the solution to cannula 13. The bulb may be composed of the same elastomeric material composing tubing 12, e.g., rubber, plastic, or silicone rubber. As more clearly shown in FIG. 1, the bulb is mounted between a pair of spaced mounting brackets 18 and 19 with bracket 18 having a recess 20 formed thereon generally conforming to the configuration of bulb 17 to aid in preventing movement of the bulb relative to the brackets in control console 16.

As further shown in FIGS. 1 and 2, a main check valve means 21 is connected in tubing 12, between source 11 and bulb 17, to permit solution flow only from the source to the bulb and to prevent reflux of the solution therepast. The check valve means may be of the rigid (e.g., ball check) or distensible (e.g., elastic-flutter) type, the latter type being composed of an elastomeric material which renders the valve volumetrically distensible. In certain system applications, a negative pressure wave may occur at the tip of cannular 13 immediately following a pulse discharge therefrom when the distensible type of check valve is used. Such phenomena may dictate the desirability to employ a second, optional check valve 22 in tubing 12 between cannula 13 and bulb 17.

It should be noted that optional check valve 22 may only be required in systems wherein cannular 13 is attached to a closed pressure transducer measuring system or the like. However, in any type system wherein main check valve 21 is of the distensible type it may provide desirable to also utilize check valve 22 to provide an additional margin of safety against negative pressure or aspiration. Normal use of pulsatile infusor system 10 will induce little, if any, negative pressure wave buildup at the tip of the cannula since the system will be continuously maintained in an open state, e.g., the infusion solution will freely flow out of the cannula during irrigation with the gravitational and hereinafter described pulsating forces applied to bulb 17 preventing any negative pressure wave buildup and resulting reflux of the solution through the cannula.

Referring to FIGS. 2 and 3, pulsatile infusor system 10 further comprises compression means 23 for intermittently compressing elastomeric bulb 17 to create a series of pulsating discharges of the solution through cannula 13. The compression means comprises a piston 24 reciprocally mounted in mounting bracket 18 with an annular head 25 being formed on the end of the piston to engage and periodically compress the bulb. If so desired, a pad or coating 26 composed of Teflon or other suitable non-abrasive material may be formed on the end of head 25, as shown in FIG. 3, to prevent scoring of the bulb upon its intermittent compression by the piston head.

As shown in FIG. 2, the compression means further comprises a crank 27 connected to piston 24 through a standard universal ball and socket connection 28. The opposite end of the crank is mounted for relative rotation on an eccentric cam plate 29, mounted on a spur gear 30 by a pin 31 secured at its lower end to the gear (FIG. 5). The spur gear is rotated to reciprocate piston 24 by an electric drive motor 32 having its output shaft 33 secured to a pinion gear 34 which meshes with an intermediate spur gear 35.

A rate control means 36, shown in the form of a rotary dial-type variable electrical transformer connected to a dial read-out on console 16, is adapted to selectively vary the rate of compression of bulb 17 by piston 24 and thus the volume of each pulse of solution discharged from cannula 13. A plug 37 is adapted to connect the transformer to a standard 110 v. wall socket and to step such voltage down to 5 v. for purposes of driving motor 32. The latter voltage can be varied to vary the number of compressions per second within the approximate range of 0-10 compressions per second, for example.

In addition to varying the rate of compression of bulb 17, it may prove desirable to also selectively vary the length of the stroke of piston 24 and thus the volume discharged through the cannula for each pulse. To this end and referring to the schematic illustration of a stroke control means in FIG. 2 and to FIG. 5, an elongated slot 39 is formed through cam 29 and has a square upper end of pin 31 closely fitted therein to provide the drive connection from the gear to the cam. The slot intersects the center of the cam and with the pin positioned at the radial outer end of the slot, as shown, the cam will effect its maximum throw on piston 24. Movement of the cam and attached crank generally leftwardly in FIG. 2 to position the pin at the radial inner end of the slot and at the center of the cam will effect a zero throw condition of operation whereby the piston will not reciprocate. Shifting of the cam in this manner may be effected by a lever 40, mounted on the front of control module or console 16 (FIG. 1), with the control lever being connected to the cam by conventional linkage, schematically illustrated at 41 in FIG. 2. Other well-known adjustable cam arrangements could be used in lieu of that shown and described herein.

Pulsatile infusion system 10 preferably also includes a force control means 42 which functions to modulate the force of the pulsating discharge of solution through the cannula. In the embodiment illustrated in FIGS. 1-3, the force control means comprises a thumb screw 43 threadably mounted on bracket 19 for purposes of selectively and adjustably applying a fixed compression on bulb 17. The end of the thumb screw engaging the bulb may also have a coat or pad 44 of non-abrasive material, such as Teflon, secured thereon. Tightening of the thumb screw to compress the volumetrically distensible chamber or reservoir of bulb 17 will form a rigid backup for the bulb so that side of the bulb will not back-away from piston 24 and expand to thus render the compression stroke of the piston more effective in forcing the column of solution out of the open end of the cannula (FIG. 3).

FIG. 4 is similar to FIG. 3, but illustrates a modification of the force control means wherein a rigid metallic jacket 45 is securely mounted between mounting brackets 18 and 19 (not shown in FIG. 4) to provide a close-fitting chamber around bulb 16 and a pair of pressure plates 46 and 47. The pressure plates, which may be composed of a rigid plastic or metal material, generally conform to substantial arcuate surface portions and contour of bulb 17 to increase the effective surface area of contact thereat. As shown, the jacket has suitable openings 48 and 49 formed therethrough to accommodate piston head 25 and the head end of a thumb screw 43, respectively.

Jacket 45 may comprise a pair of jacket sections 50 and 51 hingedly connected together by one or more hinges 52 to facilitate installation and removal of pressure plates 46 and 47. In addition, a plurality of standard snap fasteners 53 can be utilized to releasably attach the sections together. If so desired, the inner surfaces of the pressure plates contacting the bulb could be suitably coated or covered with a non-abrasive pad, such as Teflon.

MODE OF OPERATION

During the course of performing extracapsular cataract extraction, irrigation and aspiration or simple irrigation of cataractous lens material from the eye will be required. In particular, the anterior capsule of the cataractous lens is opened or removed intentionally, and the lens material, both cortex and nucleus, are removed in this manner. Pulsatile infusor system 10 will allow continuous flow irrigation which maintains the anterior chamber to have superimposed upon it fully controllable and gentle pulses of fluid which are effected to disorganize and disintegrate cortical lens material and remove that lens material from the lens capsule. The open tip of cannula 13 will stay in full view in the center of the patient3 s pupil and is used to direct the pulsatile jet of fluid towards the remaining cortical elements to break then apart and irrigate them from the eye. As indicated above, the various controls integrated into the system will enable the user to closely modulate the rate of pulses (rate control means 36), the force of the pulsating discharge (force control means 42), and the duration of each pulse (stroke control means).

Pulsatile infusion system 10 is useful in other areas in the fields of medicine and surgery, such as the continuous intravenous infusion of a liquid solution for medicinal and related purposes. A common problem arising during a continuous intravenous infusion procedure is the tendency for the infusion line to become blocked by the collection of small bloodclots at the tip of the infusing needle or cannula. During the normal course of intravenous infusion, rate control means or transformer 36 is set to its zero setting and/or control lever 30 could be set to its zero setting whereby continuous intravenous setting is effected solely by gravity flow from infusion solution source 11, through tubing 12 and bulb 17, and cannula 13. Roller clamp 15 can be adjusted to set the desired rate of gravity flow.

In order to prevent blockage caused by bloodclots at the tip of cannula 13, the system can be adjusted in the above described manner to provide gentle pulses of the solution through the cannula on a continuously controlled basis. The same sterility and closed system advantages prevalent with conventional intravenous infusion systems would be provided with system 10. System 10 thus exhibits the added advantage of selectively providing irrigational pulses to assist in keeping the intravenous line open to lower the frequency of clotted infusion lines.

EXPERIMENTAL TEST DATA

FIGS. 6A-6E graphically illustrate pressure, volume, and force phenomena which occurred during the testing of an experimental embodiment of pulsatile infusor system 10. Variable transformer 26 was connected to a standard electrical wall socket to step-down the 110 volt line voltage to a variable 5 volts in the transformer. Transformer 36 was enabled to vary the speed of motor 32 to provide a range of strokes for piston 24 or from 0-10 strokes or compressions per second. The volume of bulb 17 closely approximated 0.8 cc with cannula 13 having a 20 gauge opening.

With thumb screw 43 turned fully out, the volume of the bulb between piston strokes thus remained at 0.8 cc. When the thumb screw was turned fully in, such volume between piston strokes closely approximated 0.5 cc. The distance the solution spurted out of cannula with each piston stroke varied from 2 in. with a zero piston stroke (gravity feed only) to 30 in. per piston stroke when the thumb screw was fully in. The latter tests indicate that the force of each pulse of the discharged solution generally increased linearly upon sequential increases in the compression force applied to bulb 17 by the set screw.

The tests were conducted by applying a standard strain gauge on bulb 17 with the gauge being connected to a standard chart strip recorder. In each of the graphs the axes of ordinates depict relative pressure whereas the axes of abscissae depict time graduated in seconds. The tested system did not include stroke control means 38, but was otherwise generally of the type shown in FIGS. 1-3.

Figure 6A:
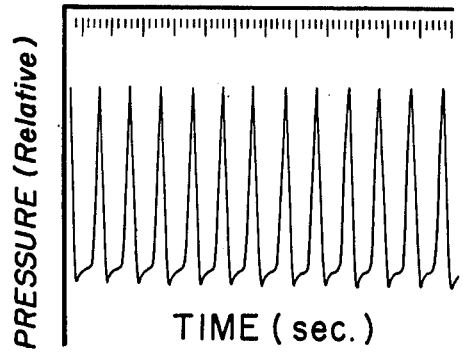
Figure 6B:
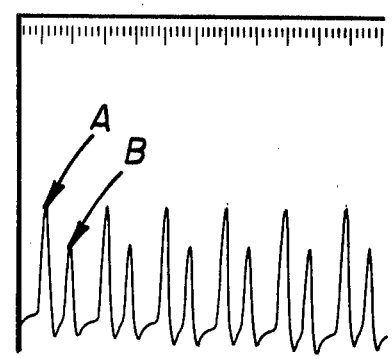

FIG. 6A represents the pressure-time relationship with tubing 12 closed by roller clamp 15 and with piston 24 being allowed to stroke to compress bulb 17. FIG. 6B illustrates the system with the tubing being open to provide open communication of the solution from source 11, through cannula 13, and with the piston stroking as indicated by compresion waves A. Background line pressure, dependent on the height of source or bottle 11 above bulb 17, is depicted by waves B.

Figure 6C:
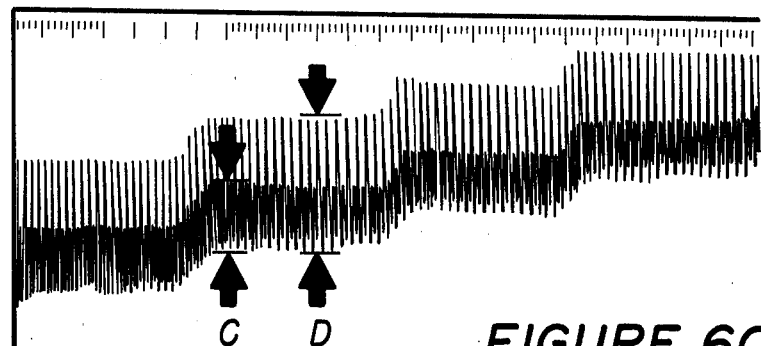

FIG. 6C depicts a system with the tubing open and with thumbscrew 43 being tightened in four sequential stages. This graph indicates that the gravity-dependent background pressure (bands C) as well as the pressure of each piston stroke is felt against bulb 17 by the strain gauge (bands D) with each remaining relatively constant regardless of thumb screw position, i.e., the bands shift upwardly for each turn of the thumb screw. In an open system, tightening of the thumb screw causes each piston stroke to empty bulb 17 more completely, i.e., the outflow volume per stroke increases. Since the time for each stroke was held constant, the force of the water jet was noted to increase, as indicated above by the 2-30 in.

range of distances the stream of solutions spurted out the cannula upon the turning-in of the thumb screw. The background pressure and flow will, of course, depend on the height that source 11 is maintained above cannula 13 and the gauge size of the cannula's opening. Changes in these two parameters will also affect the final pulse force and volume.

Figure 6D:
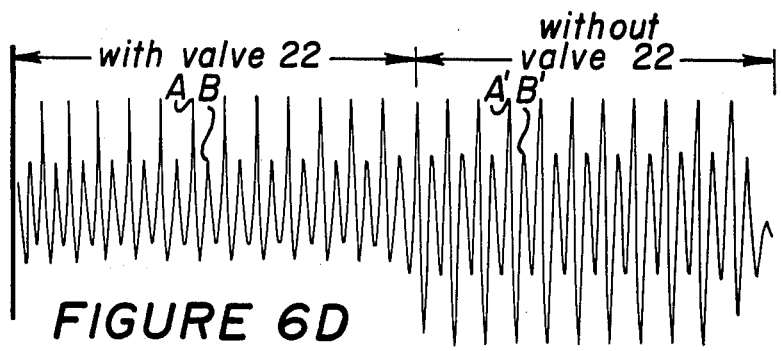
Figure 6E:
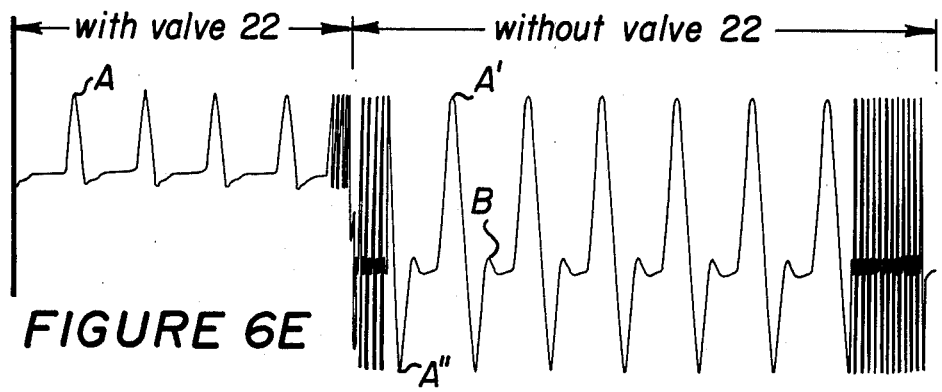

FIGS. 6D and 6E graphically illustrate tests wherein second, optional check valve 22 was added to the system, as depicted by the first portions of the curves, and then removed from the system, as depicted by the second portions of the curves. As shown in FIG. 6D, waves A represent the positive pressure waves induced by piston 24 as it compressed bulb 17 wherein waves B represent the pressure in the open line, dependent on the height of source or bottle 11 relative to cannula 13. Removal of valve 22 from the system resulted in positive pressure compression waves A', positive background pressure waves B', and additional negative waves A''. The latter waves were created in response to decompression in the tubing caused by re-expansion of bulb 17 upon retraction or destroking of the piston and possibly in some measure by the distensible nature of valve 21.

As shown in FIG. 6E, reduction in the speed of motor 32 by lowering the voltage of transformer 36 tended to spread-out the wave forms. Negative waves A'' only appear in the second portion of the curve wherein valve 22 was removed from the system.

We claim:

1. An internally sterile pulsatile infusor system comprising
   a closed, sterile source of a liquid infusion solution,
   a conduit having its first end connected to said source to receive said solution therefrom,
   a cannula connected to a second end of said conduit,
   elastic reservoir means connected in said conduit for receiving and communicating said solution to said cannula,
   check valve means in said conduit for continuously permitting solution flow only from said source to said elastic reservoir means and for preventing reflux of said solution therepast,
   compression means for intermittently compressing said elastic reservoir means to create a series of pulsating discharges of said solution through said cannula and
   rate control means for selectively varying the rate of compression of said compression means, said rate control means including variable means for varying the rate of said compressions within the approximate range of from 0 to 10 compressions per second.

2. The pulsatile infusor system of claim 1 wherein said elastic reservoir means is volumetrically distensible and further comprising force control means for modulating the force of said pulsating discharge by selectively applying a fixed compression on said elastic reservoir means.

3. The pulsatile infusor system of claim 1 wherein said variable means comprises a variable electrical transformer.

4. The pulsatile infusor system of claim 1 wherein said compression means includes a reciprocating piston positioned to periodically compress said elastic reservoir means.

5. The pulsatile infusor system of claim 4 wherein said compression means further comprises an electric drive motor connected to said rate control means, a crank connected to said piston, cam means connected to said crank for reciprocating said crank and piston upon rotation of said cam means, and drive means interconnecting said cam means and said motor.

6. The pulsatile infusor system of claim 4 further comprising stroke control means for selectively varying the length of the stroke of said piston.

7. The pulsatile infusor system of claim 1 wherein said elastic reservoir means is volumetrically distensible and further comprising force control means for modulating the force of said pulsating discharge by selectively applying a fixed compression on said elastic reservoir means.

8. The pulsatile infusor system of claim 7 wherein said force control means comprises means for adjustably applying a fixed compression on elastic reservoir means.

9. The pulsatile infusor system of claim 8 wherein said force control means comprises a set screw diametrically opposed to said compression means.

10. The pulsatile infusor system of claim 1 wherein said conduit comprises flexible tubing and wherein said elastic reservoir means comprises an elastomeric bulb connected in said tubing.

11. The pulsatile infusor system of claim 10 wherein said bulb is mounted between a pair of first and second mounting brackets and wherein said compression means comprises a piston reciprocally mounted in said first mounting bracket to periodically engage a side of said bulb.

12. The pulsatile infusor system of claim 11 further comprising force control means for modulating the force of said pulsating discharge, including a set screw threadably mounted in said second mounting bracket and diametrically opposed relative to said piston.

13. The pulsatile infusor system of claim 1 further comprising second check valve means connected in said conduit, between said cannula and said elastic reservoir means, for preventing reflux of said infusion solution from said cannula to said elastic reservoir means.

14. An internally sterile pulsatile infusor system comprising
   a closed, sterile source of a liquid infusion solution,
   a conduit comprising flexible tubing having its first end connected to said source to receive said solution therefrom,
   a cannula connected to a second end of said conduit,
   elastic reservoir means comprising an elastomeric bulb connected in said tubing for receiving and communicating said solution to said cannula, said bulb mounted between a pair of first and second mounting brackets,
   check valve means in said conduit for permitting solution flow only from said source to said elastic reservoir means, and
   compression means comprising a piston reciprocally mounted in said first mounting bracket to periodically engage a side of said bulb for intermittently compressing said elastic reservoir means to create a series of pulsating discharges of said solution through said cannula.

15. An internally sterile pulsatile infusor system comprising
   a closed, sterile source of a liquid infusion solution,
   a conduit having its first end connected to said source to receive said solution therefrom,
   a cannula connected to a second end of said conduit, elastic reservoir means connected in said conduit for receiving and communicating said solution to said cannula, check valve means in said conduit for continuously permitting solution flow only from said source to said elastic reservoir means and for preventing reflux of said solution therepast, compression means for intermittently compressing said elastic reservoir means to create a series of pulsating discharges of said solution through said cannula, and rate control means for selectively varying the rate of compression of said compression means, said compression means including a reciprocal piston positioned to periodically compress said elastic reservoir means, an electric drive motor connected to said rate control means, a crank connected to said piston, cam means connected to said crank for reciprocating said crank and piston upon rotation of said cam means, and drive means interconnecting said cam means and said motor.

16. An internally sterile pulsatile infusor system comprising a closed, sterile source of a liquid infusion solution, a conduit having its first end connected to said source to receive said solution therefrom, a cannula connected to a second end of said conduit, elastic reservoir means connected in said conduit for receiving and communicating said solution to said cannula, check valve means in said conduit for continuously permitting solution flow only from said source to said elastic reservoir means and for preventing reflux of said solution therepast, compression means for intermittently compressing said elastic reservoir means to create a series of pulsating discharges of said solution through said cannula, including a reciprocal piston positioned to periodically compress said elastic reservoir means, rate control means for selectively varying the rate of compression of said compression means, and stroke control means for selectively varying the length of the stroke of said piston.

* * * * *